United States Patent [19]

Darby

[11] Patent Number: 5,088,481
[45] Date of Patent: Feb. 18, 1992

[54] CASTED FOOT MEDICAL BOOT WITH DUAL PIVOT POINTS

[75] Inventor: H. Darrel Darby, Huntington, W. Va.

[73] Assignee: Darco International Inc., Huntington, W. Va.

[21] Appl. No.: 596,114

[22] Filed: Oct. 10, 1990

[51] Int. Cl.⁵ .................... A61F 5/04; A43B 3/12
[52] U.S. Cl. ........................ 602/23; 36/11.5; 36/102; 36/110
[58] Field of Search ........... 128/80 R, 83, 83.5, 128/84 R, 87 R, 89 R, 83.5; 36/110, 11.5, 25 R, 83, 88, 102, 103, 110, 102

[56] References Cited

U.S. PATENT DOCUMENTS

| | | | |
|---|---|---|---|
| 4,376,818 | 2/1983 | Simoglou | 36/110 X |
| 4,425,721 | 1/1984 | Spronken | 36/110 X |
| 4,631,842 | 12/1986 | Koskela | 36/103 |
| 4,677,767 | 7/1987 | Darby | 36/110 X |
| 4,773,170 | 9/1988 | Moore et al. | 36/11.5 X |
| 4,811,504 | 3/1989 | Bunke | 36/25 R X |
| 4,899,468 | 2/1990 | Richbourg et al. | 36/11.5 X |

FOREIGN PATENT DOCUMENTS 2827410 1/1980 Fed. Rep. of Germany ..... 128/83.5

Primary Examiner—Richard J. Apley
Assistant Examiner—Linda C. M. Dvorak
Attorney, Agent, or Firm—Sughrue, Mion, Zinn, Macpeak & Seas

[57] ABSTRACT

A light weight material boot specifically designed to fit a light weight fiberglass cast about the ankle and foot of a patient, has an outer sole constructed with a double rocker bottom including a first pivot point located approximately 30% over the length of the boot measured from the heel to the toe defined by an upwardly and rearwardly oblique, flat bottom surface portion and a central flat bottom surface portion on the bottom of the sole roughly below the front of the ankle and a second pivot point located approximately 70% over the length of the boot measuring from heel to toe where the metatarsal-phalangeal joint of the foot is located defined by an upwardly oblique, flat bottom surface portion from the metatarsal phalangeal joint towards the toe of the boot thereby ensuring that there is a lack of stress on the case or the lower leg and foot of the patient wearing the boot during the gait cycle.

9 Claims, 2 Drawing Sheets

CASTED FOOT MEDICAL BOOT WITH DUAL PIVOT POINTS

FIELD OF THE INVENTION

This invention relates to shoes or boots in the health care field and more specifically to a form fitting cast boot, constructed over a last and specifically designed to fit the newer, light weight, fiberglass casts, and which provides improved support for the foot utilizing a sole provided with two pivot points to ensure that the casted foot moves through the gait cycle smoothly.

BACKGROUND OF THE INVENTION

Existing cast shoes or boots are primarily designed for use with a standard, much bulkier plaster cast. Therefore, such shoes or boots are very wide, and do not contour to accommodate the bulk of the plaster casting products. These cast shoes or boots, when used with a newer, thinner, light weight fiberglass cast are much too large, preventing a good fit between the encompassing shoe upper and the fiberglass cast. Because the shoe or boot fits loosely over the cast, it is difficult for the patient to walk well and is potentially hazardous. The variety of shoes or boots in the health care field which have been built or designed to accommodate only one or more needs in that field such as; postoperative support of the feet after surgery, support of a foot carrying the bulkier plaster cast, or such foot accommodating the thinner, light weight fiberglass cast. Attempts have been made to accommodate the cast whether plaster or fiberglass, to facilitate walking and the normal gait of the wearer by providing a rocker bottom to the sole.

Patents representative of the development within these related arts, include U.S. Pat. No. 3,661,151 to Schoenbrun et al. directed to a converted shoe as an aid in the post-operative rehabilitation of a foot while serving as a splint or cast for foot fracture. The shoe is characterized by a rigid plywood mid-sole to restrict undesirable foot movement during ambulation has an open toe and eliminates the conventional tongue while employing laces to adjust or compensate for swelling of the foot. The bottom sole is ribbed with the shoe having a heel portion of the sole assembly which is thicker than that at the toe.

U.S. Pat. No. 3,848,287 to Simonson which teaches a shoe molded to the foot, has no application to the foot bearing a cast, either of the bulky plaster or the slim fiberglass type, is not formed over a last, and is devoid of a rocker bottom.

U.S. Pat. No. 4,454,871 to Mann et al. teaches a molded product replacing a plaster cast metal bracing or the like for immobilizing the ankle joint to promote healing and which facilitates immediate ambulation after application which includes a shallow V-shaped rubber sole bottom surface which may be rippled, which provides a rocker effect and in which the molded sides can be drawn together by binding straps for partially closing the opening to snugly fit the orthosis to the wearer.

U.S. Pat. No. 4,414,759 to Morgan et al. teaches an orthopedic shoe and post-operative structure having a convex bottom sole ribbed surface to simulate the natural motion of the foot in walking. A shoe upper has wrap-around straps for binding flexible side flaps in overlapping position about the top of the foot of the user and uses straps fixing to each other a VELCRO ® material at the unsecured ends of a pair of such straps secure the orthopedic shoe to the foot. The post-op shoe is limited to use after surgery to the foot and is no application to a casted foot.

In the area of casted foot protection U.S. Pat. No. 4,454,872 to Brouhard teaches a wrap-around protective device for human toes when the foot is encased in an orthopedic cast but is not a medical shoe or boot.

U.S. Pat. No. 4,677,767 to the Applicant is directed to a post-operative shoe, is devoid of a rocker sole, is not intended and normally incapable of being worn with a cast, either of plaster or the light weight fiberglass type. However, the shoe does evidence the use of overlapping flaps and VELCRO ® tipped straps for applying the post-operative shoe to the patient after surgery.

It is therefore a primary object of the present invention to provide an improved cast shoe or boot, which form fits to a cast borne by the foot of the wearer, which is constructed over a last, which is applicable to treatment of other deformities and lesions, and which contours more closely to the contour of the human foot.

It is a further object of the invention to provide a cast boot or shoe of this type, whose outer sole may be constructed of foam, is provided with a double rocker bottom, preferably a ribbed outer surface which makes use of two longitudinally spaced pivot points one of which is at the ball of the foot to ensure that the casted foot moves through the gait cycle smoothly and with the first pivot point located approximately 30% down the length of the shoe, measuring from the heel to the toe and which takes the form of roughly flat central bottom surface with upwardly oblique flat front and rear bottom surfaces.

DESCRIPTION OF THE PREFERRED EMBODIMENTS

Figure 1:
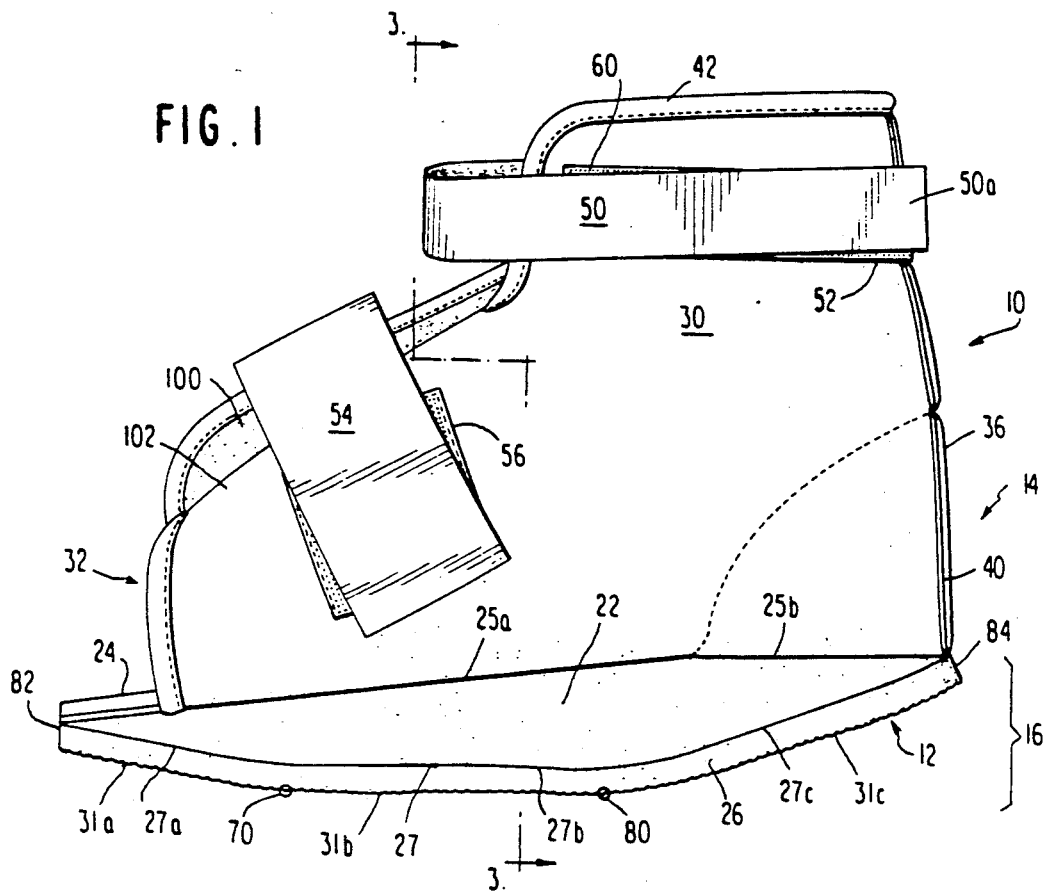
FIG. 1 is a side elevational view of a casted foot medical boot forming a preferred embodiment of the present invention.

Referring to the drawings, the casted foot medical boot or shoe of the present invention is indicated generally at 10, and includes a sole assembly indicated generally at 12 and is completed by an upper assembly or upper indicated generally at 14. The sole assembly 12 includes an outer sole 16 of a wear-resistant, resilient material such as rubber having a non-slip bottom surface with a ribbed or crepe pattern. The construction is very similar to the construction of a conventional running shoe. However, the configuration of the outer sole of the boot is significantly different from that of such running shoe. The boot upper assembly 14 is appended to the flat, composite sole assembly 12. The upper assembly 14 is secured to upper surface 22a of composite outer sole 16, top layer 22. Top layer 22 is secured at its bottom surface 22b to a full length bottom layer 26 to complete the assembly. Top layer 22 and bottom layer 26 are contoured especially as will be discussed in detail hereinafter. Both the bottom layer 26 and the top layer 22 extend the full length of the boot. The top layer 22 has a top surface 25 including a flat horizontal rear portion 25b over the rear ⅔ of the outer sole and a front assembly downwardly and forwardly oblique surface portion 25a and a bottom surface 27 including in order a front, flat downwardly and rearwardly oblique surface portion 27a, a flat horizontal itermediate surface portion 27b and an upwardly and rearwardly oblique, flat rear surface portion 27c.

The upper assembly 14 may be of a material similar to that set forth in Applicant's issued U.S. Pat. No. 4,677,767 i.e., a soft, flexible material which may be elastic and may be a composite of an outer wall of a substantially elastic, flexible material such as NYLON ® mesh and a lining of a soft, conformable material, for example, a plastic foam laminated between two layers of a sheer woven fabric mesh with the lining being bonded to the inner face of the outer wall 30. The upper assembly 14 extends along the heel and sides of the boot, with the toe of the boot being open at 32 and the upper assembly 14 lacking a tongue. A trim strip or ribbon piping as at 42 is sewn along the exposed edges of the upper assembly outer wall 30 including the edge of the single flap 100. The vertical edges of the basic two-piece upper outer wall 30, are sewn together at heel edge 104 and covered by a vertical reinforcing strip 36 which has a narrow trim strip or piping 40 over the vertical height of the same, along both sides of trim strip 36 from the sole assembly 12 to the open top 38 of upper assembly 14. Additionally, a ribbon of preferably the same soft, flexible material forming the upper assembly outer wall 30 extends completely about periphery of the sole assembly 12, including the soft inner sole 24 and overlapping the edge of the bilevel outer sole 16 and the lower end of the vertical reinforcing strip 36.

Much in the manner of my earlier U.S. Pat. No. 4,677,767 preferably, the left side outerwall 30 is extended by a flap 102 of the upper 14 which is long enough so that the free end 100a of left side flap 102 folds under the right side outer wall 30. The flap 102 may be wrapped about the dorsal portion of the foot of the patient particularly where the boot or shoe 10 is fitted to a patient whose foot is devoid of a cast permitting protection for incisions which may have been made in this region of the foot. The upper assembly 14 is thus constructed of a flexible material that molds comfortably to the contours of either the cast or the foot and ankle of the patient. The upper assembly 14 extends from above the ankle to the metatarsal phalangeal area with the open toe 32 and is also opened in front of the ankle and about the top of the foot at 38.

Figure 2:
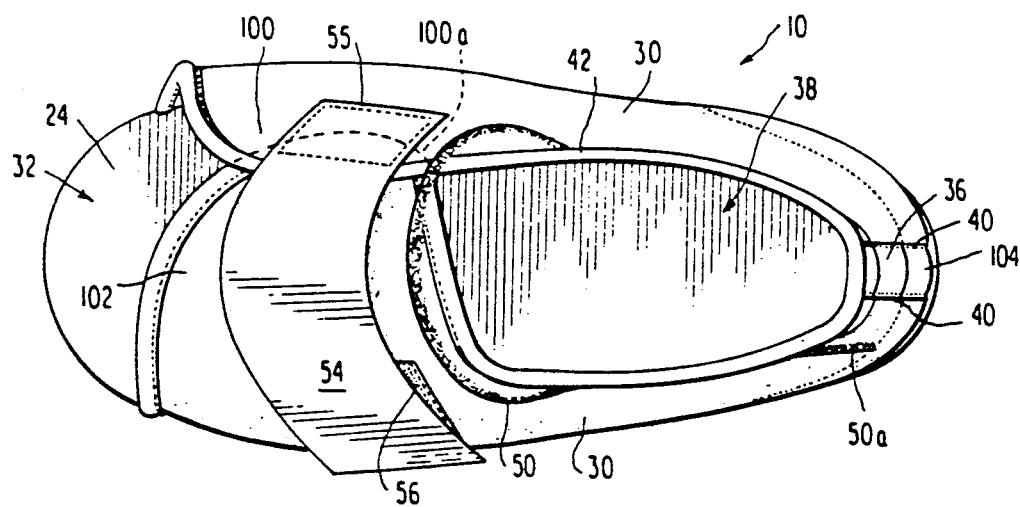
FIG. 2 is a top plan view of the casted medical boot.

The upper 14 is closed in the area of the foot overlapping flap 102 by using a single rectangular strap 54 of one type of VELCRO ® hook and loop material with that strap 54 being fixed at one end to short length flap 102 as by stitching 55 below the piping 42 on the strap 54 being of a length such that it extends over and across the face side of the right side outer wall 30. Fixed to the exterior of the left side outer wall bearing the flap 54 on the outside thereof, is a rectangular strap 56 of the opposite type hook and loop VELCRO ® material. In the illustrated embodiment, the VELCRO ® material strap 56 is of the hook type while, the VELCRO ® material strap 54 is of the loop type and with the loops on the under surface of strap 54 engaging the hooks on the outer surface of strap 56. With the exception of the adhesive bonding 25 of the bi-layer outer sole 16 and the lower edge of the upper 12 bi-layer inner sole assembly 24 to the top surface 22a and simultaneously bonding outer wall 30 between the top layer 22 of the outer sole 16, the materials making up the boot 10 are stitched to each other. The same is true for the ankle engaging closure straps 50 and 52 which are sewn in horizontal position about the ankle portion of the shoe upper 14, as best seen in FIGS. 1 and 2. Strap 50 is of extended length, more than twice the length of the shoe upper side wall 30 and being stitched to the soft, flexible material side wall 30 over the vertical reenforcing strip 36 just below the opening 38 of the shoe upper 14. In the illustrated embodiment, the loop type VELCRO ® closure strap 50 is sewn by stitches 60 to the side walls 30 of the shoe upper 12 and has a free end 50a which wraps about and over the sewn strap portion illustrated in FIG. 1 on the right side of the shoe over a considerable portion of its length at that side of the shoe. The loops of strap 50 engage the hooks of an opposite hook type short length VELCRO ® material strip 52 which strip 52 is sewn onto and simultaneously with the loop-type VELCRO ® strap 50 on the left side of the boot to the boot upper outer wall 30. The hooks of strip 52 face the loops of the free end 50a of the strap 50 so that engagement readily occurs between the hooks of the short length strip 52 and the loops of the much longer length strap 50 which wraps completely about and in overlapping fashion both side walls 30 of the boot 10. Thus, the upper 14 is made more secure by the strap 50, and strip 52 with loop and hook closures around the ankle portion of the upper 14 and cooperating with the single strap 54 extending across the top of the foot and engaging the right angle positioned opposite type strip 56 of VELCRO ® material. As may be appreciated from the description set forth above, the boot 10 is purposely designed to be narrower than known cast shoes and is contoured to snugly fit fiberglass casts which are thin, and conform to the foot of the patient.

The upper 14 is thus designed of a fabric in combination with other materials readily to contour to either a fiberglass cast or to the foot and ankle of the patient and the material has some elasticity. The boot is characterized by the utilization of highly fashionable neon shoe colors designed to compliment the new color cast materials forming fiberglass casts which have recently come into vogue. Of course, in addition, the boot is designed to be worn without a cast to aid in the healing process following surgery, trauma or to aid in the treatment of ulcerations, infections or other bony and soft tissue abnormalities.

Figure 3:
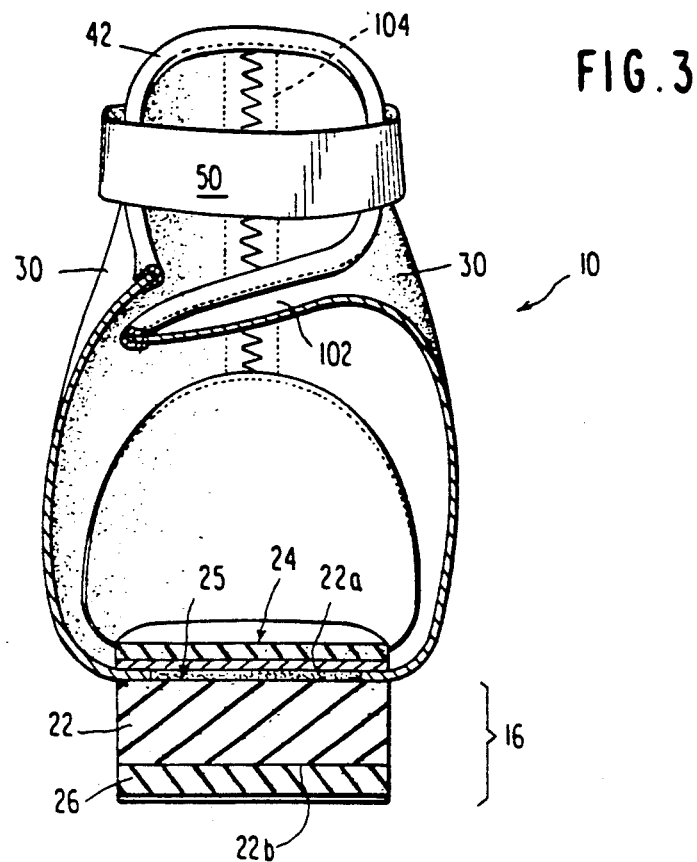
FIG. 3 is vertical, transverse sectional view through an enlarged section of the boot sole.
Figure 4:
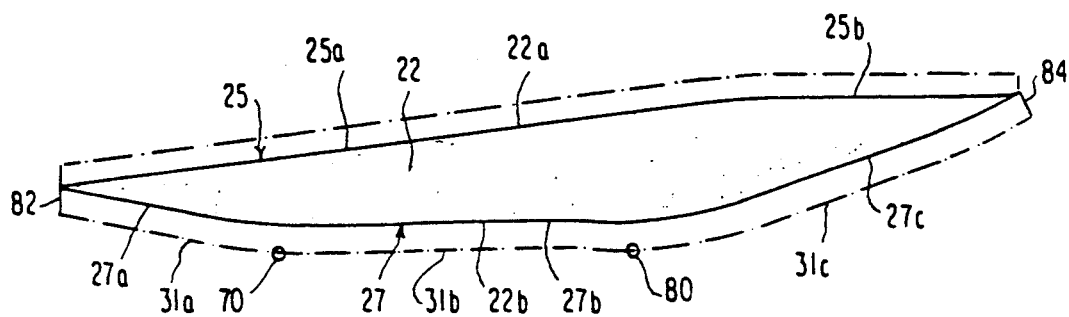
FIG. 4 is a schematic outline of the sole assembly of the casted medical boot of FIG. 1 illustrating the location of the first and second pivot points of the rocker sole construction and the typical relative dimensions of those points from the heel of the boot.

One of the key aspects of the improved cast/medical boot or shoe 10 is the provision of a double rocker bottom which permits near normal rocking motion of the foot through the gait cycle when the foot and ankle are immobilized in a cast and incapable of flexing to any degree. The boot structure is also utilized to limit motion and protect the non-casted foot with infections, injuries, etc. to the forefoot. By reference to FIG. 4, it is seen that in a typical cast boot 10 for an outer sole assembly 16 having a total sole length L=22.5 centimeters, to ensure that the casted foot moves through the gait cycle smoothly, two pivot points are made available instead of the traditional single pivot point rocker bottom. The first pivot point 80 is located approximately 30% down the length of the shoe measuring from the heel point 84 to the toe point 82 over distance 27c where oblique bottom surface 31c meets flat center bottom surface 31b on the bottom of the outer sole at 80, FIG. 3, in vertical alignment with the front of the ankle. A second pivot point 70 is located approximately 72% down the length of the shoe, over length 27b of the flat bottom surface 31b again measuring from the heel 84 in the direction of toe 82, FIG. 5, or in vertical alignment with the metatarsal-phalangeal (m-p) joint of its patients foot. This second pivot point 70 takes a sharp angle upward away from the m-p joint over distance 27b towards the toe end 82. The combination of pivots 70, 80 ensures that there is no stress on the cast itself or on the lower leg and foot of the patient wearing the shoe 10 during the gait cycle.

It should be understood that while a preferred embodiment of the invention has been shown and described herein, changes and additions may be made therein without departing from the spirit of the invention. Reference should, accordingly, be had to the appended claims in determining the scope of the invention.

I claim:

1. A medical boot capable of conforming to a form fitting cast, enveloping a foot and ankle of a patient, said boot comprising:

a sole assembly, an upper assembly secured to said sole assembly and adapted to surround the heel, sides and dorsal portions of the patient's foot while leaving the toe region open, said upper assembly including a pair of side walls of flexible material which mold comfortably to the contours of either the cast or the foot and ankle of the patient, one of said upper assembly side walls including a flap which underlies the other side wall and is adapted to cover the dorsal region of the foot, said sole assembly comprising an outer sole extending generally the length of the shoe, from heel to toe, having an outer sole bottom surface which tapers from the toe and heel oppositely in directions away from the upper, wherein said outer sole bottom surface includes a flat horizontal central portion and a flat rearwardly, upwardly oblique portion forming therebetween a first pivot point for said medical boot, at a position, which is in vertical alignment with the front of the ankle of the patient, and wherein, said bottom of said outer sole includes a forwardly and upwardly oblique, flat portion from the end of the flat horizontal central portion remote from the heel, to the toe defining therebetween a second pivot point in vertical alignment with the metatarsal-phalangeal joint is located on the foot of the patient borne by said shoe, and an outer sole top surface which is flat and which tapers forwardly and downwardly over the flat central portion and said upwardly oblique flat portion of the sole bottom surface from the central portion to the toe, whereby; the combination of said two pivot points ensures that there is no stress on the cast or on the lower leg and foot of the patient during the gait cycle upon ambulation of the patient.

2. The medical boot as claimed in claim 1, wherein said outer sole is formed of a top layer of substantial thickness and having oppositely tapered portions respectively in the direction of the heel and toe of the outer sole, wherein the upper surface of the top layer is joined to the shoe upper assembly, and wherein said bottom layer is generally of even thickness over the longitudinal length of the same and wherein, said bottom layer extends the full length of the sole assembly from the heel to the toe thereof of the boot.

3. The medical boot as claimed in claim 1, wherein said top layer, and said bottom layer are adhesively bonded to each other, and wherein the boot upper is adhesively bonded to the upper surface of said outer sole top layer.

4. The medical boot as claimed in claim 2, wherein said top layer, and said bottom layer are adhesively bonded to each other, and wherein the boot upper is adhesively bonded to the upper surface of said outer sole top layer.

5. The medical boot as claimed in claim 2, wherein the bottom surface of the outer sole is corrugated over the length of the same with the corrugations extending transversely of the longitudinal axis of the boot.

6. The medical boot as claimed in claim 1, wherein the first pivot point is located approximately 30% of the length of the boot measuring from the heel to the toe.

7. The medical boot as claimed in claim 1, wherein said second pivot point is located approximately 70% over the length of the boot measuring from the heel to the toe.

8. The medical boot as claimed in claim 5, wherein said second pivot point is located approximately 70% over the length of the boot measuring from the heel to the toe.

9. The medical boot as claimed in claim 1, wherein said shoe further comprises two sets of closure straps formed of face contacting portions of opposite hook and loop engaging material straps about the flexible side walls of the shoe upper assembly extending horizontally and wrapped about the ankle of the shoe, and extending obliquely across the underlying flap about the dorsal portion of the foot respectfully, to maintain the side walls of the flexible material upper assembly securely wrapped about the patient's foot and about the ankle thereof from heel to toe to ensure that the casted foot moves through the gait cycle smoothly while making use of the two pivot points provided on the bottom surface of the sole assembly outer sole.

* * * * *